(12) United States Patent
Sherbine et al.

(10) Patent No.: US 7,442,792 B2
(45) Date of Patent: *Oct. 28, 2008

(54) PROCESS FOR THE PREPARATION OF PYRAZOLO[1,5-A]-1,3,5-TRIAZINES AND INTERMEDIATES THEREOF

(75) Inventors: James P. Sherbine, Voorhees, NJ (US); Shawn K. Pack, Plainsboro, NJ (US); Jaan A. Pesti, Yardley, PA (US); Robert E. Yule, Green Oaks, IL (US); Kenneth C. McNulty, West Chester, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/717,440

(22) Filed: Mar. 13, 2007

(65) Prior Publication Data

US 2007/0161790 A1  Jul. 12, 2007

Related U.S. Application Data

(62) Division of application No. 10/985,236, filed on Nov. 10, 2004, now Pat. No. 7,208,596.

(60) Provisional application No. 60/525,050, filed on Nov. 25, 2003.

(51) Int. Cl.
 C07D 487/04 (2006.01)
 A61K 31/53 (2006.01)
 A61P 3/04 (2006.01)
 A61P 9/12 (2006.01)
 A61P 25/22 (2006.01)

(52) U.S. Cl. .................. 544/180; 544/217; 544/220

(58) Field of Classification Search .............. 544/180, 544/217, 220

See application file for complete search history.

(56) References Cited

U.S. PATENT DOCUMENTS

| 3,910,907 | A | 10/1975 | O'Brien et al. | 260/248 |
|---|---|---|---|---|
| 4,824,834 | A | 4/1989 | Fujii et al. | 514/246 |
| 4,892,576 | A | 1/1990 | Kriiger et al. | 71/93 |
| 5,137,887 | A | 8/1992 | Hashimoto et al. | 514/246 |
| 5,484,760 | A | 1/1996 | Bussler et al. | 504/103 |
| 6,060,478 | A | 5/2000 | Gilligan et al. | 514/258 |
| 6,124,289 | A | 9/2000 | He et al. | 514/245 |
| 6,136,809 | A | 10/2000 | Gilligan et al. | 514/258 |
| 6,191,131 | B1 | 2/2001 | He et al. | 514/246 |
| 6,271,376 | B1 | 8/2001 | Saikali et al. | 544/320 |
| 6,313,124 | B1 | 11/2001 | He et al. | 514/246 |
| 6,358,950 | B1 | 3/2002 | He et al. | 514/246 |
| 6,716,981 | B2 | 4/2004 | Saikali et al. | 544/320 |
| 7,208,596 | B2 * | 4/2007 | Sherbine et al. | 544/180 |
| 2003/0125330 | A1 | 7/2003 | Gilligan | 514/246 |

FOREIGN PATENT DOCUMENTS

| CN | 1 088 574 | 6/1994 |
|---|---|---|
| EP | 0 269 859 A2 | 6/1988 |
| EP | 0 594 149 A3 | 4/1994 |
| JP | 2001-302658 | 10/2001 |
| WO | WO 98/03510 | 1/1998 |
| WO | WO 98/08847 A1 | 3/1998 |
| WO | WO 01/23388 A3 | 4/2001 |
| WO | WO 02/072202 A1 | 9/2002 |

OTHER PUBLICATIONS

Albert, A.H., et al., "Synthesis of 2,4-dimethylpyrazolo[1,5-a]-1,2,5-triazine," *J. Het. Chem.*, 1973, p. 885.

Battaglia, G., et al., "characterization of corticotrophin-releasing factor receptor-mediated adenylate cyclase activity in the rat central nervous system," *Synapse*, 1987, 1, 572-581.

Bellec, C., et al., "Structure de derives de β- cétonitriles. II. Tautomérie hydrazone-énehydrazine; etude des configurations," *Beilstein Institut. Zur Foerderung Der*, Accession No. 3384927, 1988, II-441-II-448 (Summary in English).

Beyer, H., et al., "Zur umsetzung von ketonitrilen mit hydrazinderivaten der kohlensäure," *Verlag Chemie GMBH Weinheim/Bergstr.*,, 1960, 9, 2209-2216.

Boissier, J.-R., et al., "A new method for rapid screening of minor transquillizers in mice," *Eur. J. of Pharmacol.*, 1968, 4, 145-151.

Bruni, F., et al., "Reactivity of 7-(2-dimethylaminovinyl)pyrazolo[1,5-a]pyrimidines: synthesis of pyrazolo[1,5-a][3,4-e]pyrimidine derivatives as potential benzodiazepine receptor ligands. 2.," *J. Heterocycl. Chem.*, 1995, 32, 291-298.

(Continued)

*Primary Examiner*—Venkataraman Balasubram
(74) *Attorney, Agent, or Firm*—John F. Levis; Shah R. Makujina; Woodcock Washburn LLP

(57) ABSTRACT

The present invention provides novel processes and intermediates for preparing corticotropin releasing factor (CRF) receptor antagonists having the structure below which are useful in treating CRF-related disorders such as anxiety and depression.

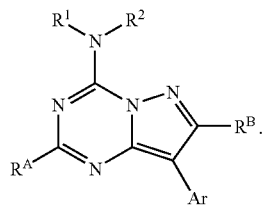

18 Claims, No Drawings

OTHER PUBLICATIONS

Collington, E.W., et al., "A facile and specific conversion of allylic alcohols to allylic chlorides," *J. Org. Chem.*, 1971, 36(20), 3044-3196.

Crossland, R.K., et al., "A facile synthesis of methanesulfonate esters," *J. Org. Chem.*, 1970, 35(9), 3195-3196.

Cusmano, S., et al., "Comportamento dei legami lidenici verso alcuni reattivi. Struttura delle sostanze ottenute per azione della semicarbazide sui benzalderivati di corpi β-chetonitriliei—Nota V.," *Gazz. Chim. Ital.*, 1952, 82, 373-384 (Italian).

Dunn, A.J., et al., "Physiological and behavioral responses to corticotrophin-releasing factor administration: is CRF a mediator of anxiety or stress responses," *Brain Res. Rev.*, 1990, 15, 71-100.

Funk, D., et al., "Role of catecholamines in the frontal cortex in the modulation of basal and stress-induced autonomic output in rats," *Brain Res.*, 1996, 741, 220-229.

Griebel, G., et al., "Genetic differences in the mouse defense test battery," *Aggress. Behav.*, 1997, 23, 19-31.

Grigoriadis D.E., et al., "Corticotropin-releasing factor (CRF) receptors in intermediate lobe of the pituitary: biochemical chjaracterization and autoradiographic localization," *Peptides*, 1989, 10, 179-188.

He, L., et al., "4-(1,3-dimethoxyprop-2-ylamino)-2,7-dimethyl-8-(2,4-dichlorophenyl)-pyrazolo[1,5-*a*]-1,3,5-triazine: a potent, orally bioavailable $CRF_1$ receptor," *J. Med. Chem.*, 2000, 43, 449-456.

Kobe, J., et al., "The chemistry of 4-hydrazino-7-phenylpyrazolo[1,5-a]-1,3,5-triazines," *J. Het. Chem.*, 1974, 991-996.

Kobe, J., et al., "The synthesis and chemical reactions of certain pyrazolo[1,5-a]-1,3,5-triazines(1)," *J. Het. Chem.*, 1974, 199-204.

Logemann, W., et al., "Studien in der heterocyclischen reihe, II. Mitteil.*): Die synthese von 1.3.5-triazine und 5-oxy-isoxazol-derivaten," *Chem. Ber.*, 1954, 87, 1175-1179 (German).

Meyers, A.I., et al., "An efficient total synthesis of propylure, the highly active sex attractant for the pink bollworm moth," *Tetrahedron*, 1971, 27, 5979-5985.

Misslin, R., et al., "Behavioural validation of a light/dark choice procedure for testing anti-anxiety agents," *Behav. Process*, 1989, 18, 119-132.

Munson, P.J., et al., "Ligand: A versatile computerized approach for characterization of ligand-binding systems," *Anal. Biochem.*, 1980, 107, 220-239.

Nagel, D.L., et al., "Synthesis of alkyl-substituted benzo[c]phenanthrenes and chrysenes by photocyclization," *J. Org. Chem.*, 1977, 42(22), 3626-3628.

Nishida, A., et al., "Rotational isomerism in fluorine derivatives XIV conformational equillbria of β-substituted 9-(2-cyanomethylphenyl) fluorine derivatives," *Technol. Rep. Yamaguchi Univ.*, 1988, 4(2), 145-150.

Novinson, T., et al., "synthesis of unsymmetrical 2,4-dialkylpyrazolo[1,5-a]-1,3,5-triazines," *J. Het. Chem.*, 1974, 691-695.

Pellow, S., et al., "Validation of open: closed arm entries in an elevated plus-maze as a measure of anxiety in the rat," *J. of Neurosci. Methods*, 1985, 14, 149-167.

Page, G.A., et al., "The synthesis of benzcyclohepten-6-one," *J. Am. Chem. Soc.*, 1953, 75, 2053-2055.

Pietraszuk, C., et al., "Cross-metathesis of vinylsilanes with olefins in the presence of Grubbs' catalyst," *Tetrahedron Lett.*, 2001, 42, 1175-1178.

Porsolt, R.D., et al., "Depression: a new animal model sensitive to antidepressant treatment," *Nature*, 1977, 266, 730-732.

Principles of Process Research and Chemical Development in the Pharmaceutical Industry, *Wiley*, 1998, p. 38-40.

Rapoport, H., et al., "The synthesis of 2,3,4-trimethoxybenzcyclohepten-6-one," *J. Am. Chem. Soc.*, 1951, 73, 2239-2241.

Senga, K., et al., "Synthesis and enzymic activity of various substituted pyrazolo[1,5-a]-1,3,5-triazines as adenosine cyclic 3',5'-phosphate phosphodiesterase inhibitors," *J. Med. Chem.*, 1982, 25, 243-249.

Souchay, et al., "CHDCAQ," *S.R.Hebd. Seances Acad. Sci. Ser. C*, 1973, p. 1457 (Accession No. 2981462, 1 page).

Stogryn, E.L., "A new synthesis of 3,4-(difluoromethylenedioxy)benzaldehydr," *J. Org. Chem.*, 1972, 37(4), p. 673.

Vogel, J.R., et al., "A simple and reliable conflict procedure for testing anti-anxiety agents," *Psychopharmcologia (Berl.)*, 1971, 21, 1-7.

Willner, P., et al., "An animal model of anhedonia," *Clin. Neuropharmacol.*, 1992, 15(supp. 1), 550A-551A.

Wynn, P.C., et al., "Regulation of corticotrophin-releasing factor (CRF) receptors in the rat pituitary gland: effects of adrenalectomy on CRF receptors and corticotroph responses," *Endocrinology*, 1985, 116(4), 1653-1659.

Yamashita, M., "*BCSJA8,*" *Bull. Chem. Soc. Jpn.*, 1941, 16, 413-415 (Accession No. 3384927, 1 page).

Kazimierczuk, Z. et al., "Total synthesis of certain 2-, 6-mono- and 2,6-disubstituted-tubercidin derivatives. Synthesis of tubercidin via the sodium salt glycosylation procedure," *Nucleic Acids Research*, 1984, 12(2), 1179-1192.

\* cited by examiner

US 7,442,792 B2

PROCESS FOR THE PREPARATION OF PYRAZOLO[1,5-A]-1,3,5-TRIAZINES AND INTERMEDIATES THEREOF

CROSS-REFERENCE TO RELATED APPLICATIONS

This application is a divisional of application Ser. No. 10/985,236, filed Nov. 10, 2004, now U.S. Pat. No. 7,208,596, which claims priority to Provisional Application Ser. No. 60/525,050, filed Nov. 25, 2003, the disclosures of which are incorporated herein by reference in their entireties.

FIELD OF THE INVENTION

The present invention relates to novel processes amenable to large scale preparation of pyrazolo[1,5-a]-1,3,5-triazines.

BACKGROUND OF THE INVENTION

Corticotropin releasing factor (CRF), synonymous with corticotropin releasing hormone (CRH), is a 41 amino acid peptide that coordinates the overall response of the body to stress. As an agonist of CRF receptors (e.g., $CRF_1$, and $CRF_2$), CRF is well known as the primary physiological secretagogue controlling hypothalamic-pituitary-adrenal (HPA) axis activity which mediates the endocrine stress response. CRF also plays a central role in the autonomic and behavioral responses to stress. Variation in physiological levels of CRF has been correlated with various disorders including depression and anxiety.

Antagonists of CRF receptors have been shown to effectively ameliorate behavioral stress responses in animal models. It is well established that systemic administration of $CRF_1$ receptor antagonists leads to anxiolytic and antidepressant effects in rodents. Animal model evidence also shows that $CR_1$ antagonists can help alleviate the symptoms of drug withdrawal, stress-induced seizures, and certain inflammations. A role for CRF has also been postulated in the etiology and pathophysiology of Alzheimer's disease, Parkinson's disease, Huntington's disease, progressive supranuclear palsy, and amyotrophic lateral sclerosis as they relate to the dysfunction of CRF neurons in the central nervous system. Eating disorders, such as anorexia nervosa, have also been linked to elevated levels of CRF.

Though widely dispersed throughout the central nervous system, CRF receptors are also found in peripheral systems including glandular, vascular, gastrointestinal, and immune system tissues. Accordingly, CRF antagonists are believed to have potential in treating numerous other disorders outside the central nervous system. Some CRF-related disorders of peripheral systems include, for example, hypertension, tachycardia, congestive heart failure, stroke, irritable bowel syndrome, post-operative ileus, and colonic hypersensitivity. Studies have indicated that $CRF_1$ antagonists may also be useful-as hair growth stimulators.

Pyrazolo[1,5-a]-1,3,5-triazine derivatives have been identified as potent $CRF_1$ antagonists and are currently being studied as therapeutic agents for treatment of various CRF-related disorders, including many of those mentioned above. Numerous pyrazolotriazine $CRF_1$ antagonists have been reported in, for example, U.S. Pat. Nos. 6,124,289; 6,191,131; 6,313,124; 6,060,478; 6,136,809; and 6,358,950, as well as WO 02/72202 and WO 98/08847.

Preparation of pyrazolo[1,5-a]-1,3,5-triazine compounds typically involves a multi-step procedure including two ring-forming reactions to produce the bicyclic core. Syntheses of various pyrazolo[1,5-a]-1,3,5-triazine compounds are reported in the above references as well as in WO 01/23388; U.S. Pat. Nos. 4,824,834, 3,910,907, 5,137,887, 4,892,576, and 5,484,760; EP 594149; He et al., *J. Med. Chem.*, 2000, 43, 449; Senga, et al., *J. Med. Chem.*, 1982, 25, 243; Bruni, et al., J. Heterocycl. Chem., 1995, 32, 291; Kobe, et al., *J. Het. Chem.*, 1974, 991; Kobe, et al., *J. Het. Chem.* 1974, 199; Novinson, et al., *J. Het. Chem.*, 1974, 691; and Albert, et al., *J. Het. Chem.* 1973, 885. Ring-forming and other reactions are reported in Beyer, et al., *Ber.*, 1960, 93, 2209 and Cusmano, et al., *Gazz. Chim. Ital.*, 1952, 82, 373.

Numerous active pyrazolo[1,5-a]-1,3,5-triazine compounds include a multi-substituted aryl or heteroaryl group attached to the 8-position of the bicyclic core. Introduction of the 8-subsituent often involves the use of an aryl or heteroaryl acetonitrile derivative. Methods for preparing aryl or heteroaryl acetonitrile derivatives from the corresponding halomethyl compound and cyanide are reported in JP 2001302658; CN 1088574; and Nishida, et al., *Technol. Rep. Yamaguchi Univ.*, 1988, 4(2), 145. Other references reporting reactions that can be used in the preparation of aryl or heteroaryl acetonitrile derivatives include, for example, Nagel, et al., *J. Org. Chem.*, 1977, 42, 3626 and Stogryn, *J. Org. Chem.*, 1972, 37, 673 (n-BuLi metallation of aryl bromides and condensation with DMF to form aldehydes); Li, et al., *Tetrahedron Lett.* 2001, 1175 (sodium borohydride reduction of benzyl aldehydes to benzyl alcohols); *J. Org. Chem.*, 1970, 35, 3195, *J. Org. Chem.*, 1971, 36, 3044, *Tetrahedron* 1971, 27, 5979 (chlorination of benzyl alcohol with mesyl chloride and base); *J. Am. Chem. Soc.*, 1951, 73, 2239, *J. Am. Chem. Soc.*, 1953, 75, 2053 (conversion of benzyl chloride to cyanide derivative); and Repic, *Principles of Process Research and Chemical Development in the Pharmaceutical Industry*, Wiley, 1998, p. 38.

In view of the importance of pyrazolo[1,5-a]-1,3,5-triazine derivatives in the treatment of CRF-related disorders such as anxiety and depression, improved methods for their synthesis are needed. Such improvements can include, for example, enhanced enantiomeric and/or diastereomeric selectivity in individual reaction steps, enhanced chemical purity, increased yields, employment of lower cost starting materials, employment of less toxic starting materials, lowered energy consumption (e.g., avoidance of reactions conducted at very high or low temperatures or pressures), reduction in the number of synthetic steps, and improved scale-up conditions. The processes and intermediates discussed herein help fulfill these and other needs.

SUMMARY OF THE INVENTION

The present invention provides, inter alia, processes and intermediates for preparing pyrazolo[1,5-a]-1,3,5-triazines of Formula I below which are CRF receptor antagonists useful for treating CRF-related disorders including anxiety and depression.

The present invention further provides processes and intermediates for preparing aryl and heteroaryl acetonitrile compounds useful as intermediates in preparing pyrazolo[1,5-a]-1,3,5-triazines of Formula I.

DETAILED DESCRIPTION OF PREFERRED EMBODIMENTS

The present invention provides, inter alia, processes for preparing pyrazolo[1,5-a]-1,3,5-triazines of Formula I:

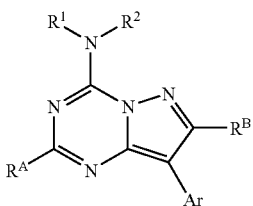

wherein:
  Ar is phenyl or pyridyl substituted with 0 to 5 $R^3$;
  each $R^1$ and $R^2$ is, independently, H, $(C_1$-$C_8)$alkyl, or $(C_1$-$C_6)$alkoxyalkyl;
  each $R^3$ is, independently, H, halo, CN, nitro, $(C_1$-$C_4)$alkyl, $(C_1$-$C_4)$alkoxy, $(C_1$-$C_4)$haloalkyl, or $(C_1$-$C_4)$haloalkoxy; and
  each $R^A$ and $R^B$ is, independently, $(C_1$-$C_4)$alkyl. In some embodiments, either or both $R^A$ and $R^B$ are methyl. In further embodiments, Ar can be 2-methyl-4-methoxyphenyl, 2-chloro-5-fluoro-4-methoxyphenyl, or 2-methyl-6-methoxypyrid-3-yl. In yet further embodiments, both $R^1$ and $R^2$ can be methoxyethyl, or $R^1$ is H and $R^2$ is pent-3-yl, or $R^1$ is H and $R^2$ is but-2-yl.

According to the present invention the processes of preparing compounds of Formula I can comprise the steps:
(a) contacting a compound of Formula III:

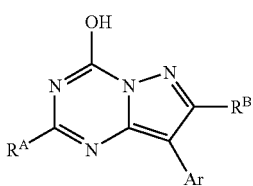

with $POX_3$ in the presence of an amine, preferably a sterically encumbered amine, selected from diisopropylethylamine, diethylphenylamine, diisopropylaniline, diethylaniline, diisopropylisobutylamine, tribenzylamine, triphenylamine, tricyclohexylamine, diethylisopropylamine wherein X is halo, for a time and under conditions sufficient to provide a compound of Formula II:

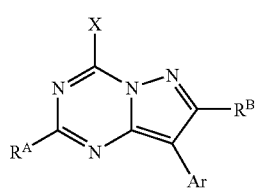

and;
(b) contacting the compound of Formula II with $NHR^1R^2$ for a time and under conditions sufficient to provide the compound of Formula I.

The reaction of step (a) involves the replacement of a hydroxyl moiety in the intermediate of Formula III with a halogen moiety derived from the reagent $POX_3$. Example $POX_3$ reagents include $POF_3$, $POCl_3$, $POBr_3$, and the like. In some embodiments, X is Cl. The amine step (a) can serve as catalyst for halogenation. Suitable amines are typically bulky tertiary amines selected from, for example, diisopropylethylamine, diethylphenylamine, diisopropylaniline, diethylaniline, diisopropylisobutylamine, tribenzylamine, triphenylamine, tricyclohexylamine, diethylisopropylamine. In some embodiments, diisopropylethylamine is used as the amine catalyst. The molar ratio of amine catalyst to $POX_3$ can be about 1:1.

In some embodiments, the contacting of step (a) is carried out in the presence of an ammonium salt which can act as a phase transfer agent. Any ammonium salt is suitable. Some example ammonium salts include benzyltriethylammonium chloride, benzyltributylammonium chloride, Adogens® (methyltrialkyl($C_8$-$C_{10}$)ammonium chloride). In some embodiments, the ammonium salt is benzyltriethylammonium chloride. The ammonium salt can be provided in a catalytic amount. Example amounts of ammonium salt are less than 1 eq (versus the compound of Formula III).

The contacting of step (a) can be carried out in any solvent that is non-reactive under the reaction conditions. Preferred solvents for this transformation are methyl t-butyl ether, acetonitrile, isopropylacetate, toluene and 1-chlorobutane. Suitable reaction conditions can include ambient pressure and temperatures of about 50 to about 110° C., preferably about 50 to about 70° C.

The reaction of step (b) involves the replacement of a halogen moiety in intermediates of Formula II with an amine moiety. Any primary or secondary amine is suitable, such as an amine having the formula $NHR^1R^2$. Amine can be provided in an excess amount relative to the compound of Formula II (or Formula III). Some amines of formula $NHR^1R^2$ can include, for example,

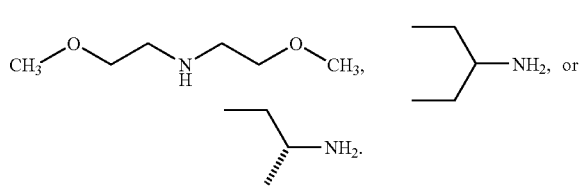

Any suitable solvent can be used to carry out the reaction of step (b). According to some embodiments, the reaction of step (b) is carried out in organic solvent. Some example organic solvents include methyl t-butyl ether, acetonitrile, isopropyl acetate, toluene, and 1-chlorobutane. In some embodiments, the organic solvent comprises either or both acetonitrile and methyl t-butyl ether, such as a mixture of acetonitrile and methyl t-butyl ether. An example acetonitrile:methyl t-butyl ether v/v ratio can be about 1:4. The reaction of step (b) can be carried out under ambient pressure and temperature. An example temperature can be from about 0 to about 50° C.

In some embodiments, the intermediate of Formula II can be reacted in situ and is not isolated prior to carrying out the reaction of step (b).

The present invention further provides processes for a first ring closure wherein a compound of Formula III is prepared by (c) contacting a compound of Formula IV:

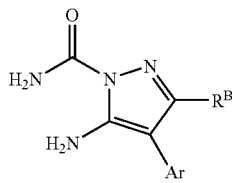

IV with $(R^4)C(OR^4)$, wherein $R^4$ is $(C_1-C_4)$alkyl, for a time and under conditions sufficient to provide the compound of Formula III. A suitable amount of $(R^4)C(OR^4)$ can be about 1 equivalent or more (versus the compound of Formula IV).

The above first ring closure process can be carried out in the presence or absence of catalytic acid or base. The reaction is typically carried out in an organic solvent. Some suitable solvents include acetonitrile, 1-methyl-2-pyrrolidinone or tetrahydrofuran. In the absence of acid or base, suitable temperatures for carrying out the first ring closure reaction are typically elevated (e.g., greater than room T, such as greater than about 25° C.). Example elevated temperatures can range from about 30 to about 100° C., or 50 to about 100° C., or about 75 to about 100° C.

An acid may be suitable for catalyzing the first ring closure reaction. Example acids include p-toluensulfonic acid (pTSA), methanesulfonic acid, sulfuric acid, and acetic acid. In some embodiments, pTSA is used as an acid catalyst. Suitable temperatures for carrying out the acid catalyzed reaction can range from about 40 to about 100, about 40 to about 70, or about 40 to about 60° C.

According to some embodiments, the first ring closure reaction is carried out in a mixture of 1-methyl-2-pyrrolidinone and pTSA. In other embodiments, the reaction can be carried out in acetonitrile.

In further embodiments, the reagent $(R^4)C(OR^4)$ can be trimethyl orthoacetate (where both $R^A$ and $R^4$ are methyl) or triethyl orthoacetate.

The present invention further provides processes for a second ring closure wherein a compound of Formula IV is prepared by (d) contacting a compound of Formula V:

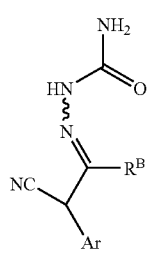

V with base for a time and under conditions sufficient to provide the compound of Formula IV. The base can be provided in any suitable amount, such as one equivalent or less (versus the compound of Formula V).

Any base can be suitable for carrying out the above processes for a second ring closure reaction. Preferred example bases include hydroxides, amines, 1,5-diazabicyclo[4.3.0]-non-5-ene and imidazole. Less preferred examples include alkoxides. In some embodiments, the base is 1,8-diazabicyclo[5.4.0]undec-7-ene (DBU).

The above second ring closure reaction can be carried out in organic solvent. Suitable organic solvents include acetonitrile, 1-methyl-2-pyrrolidinone, tetrahydrofuran, aqueous isopropyl alcohol or mixtures thereof. In some embodiments, the solvent includes 1-methyl-2-pyrrolidinone or acetonitrile.

Suitable temperatures for carrying out the second ring closure reactions can include lowered temperatures, such as temperature below room T (e.g., below 25° C.), as well as temperatures ranging from about 0 to about 30° C. Example temperatures can range from about −20 to about 20, about −10 to about 10, about 0 to about 10, about 10 to about 20, about 20 to about 30, or about 30 to about 35° C. Ambient pressure is also suitable.

The present invention further provides semicarbazone-forming processes wherein a compound of Formula V is prepared by (e) contacting a compound of Formula VI:

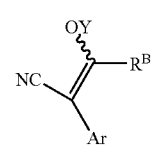

VI wherein Y is an alkali metal or $Z^1Z^2$, wherein $Z^1$ is halo and $Z^2$ is an alkaline earth metal, with semicarbazide, or acid addition salt thereof, for a time and under conditions sufficient to provide said compound of Formula VI. In some embodiments, the semicarbazide is provided as semicarbazide hydrochloride. The semicarbazide can be provided in an amount greater than about one equivalent (versus the compound of Formula VI or VII).

According to some embodiments of the above semicarbazone-forming processes, Y is an alkali metal such as K. In other embodiments, Y is $Z^1Z^2$ such as, for example, MgBr.

In further embodiments, the above semicarbazone-forming processes are carried out at a pH of from about 1 to about 6, and more preferably from about 3 to about 5. Accordingly, the contacting of step (e) can be carried out in the presence of acid such as acetic acid, hydrochloric acid, sulfuric acid, propionic acid, or butyric acid. In some embodiments, the acid is acetic acid.

In yet further embodiments, the above semicarbazone-forming processes can be carried out in aqueous solvent. Additionally, the aqueous solvent can include alcohol such as, for example, isopropyl alcohol, methyl alcohol, ethyl alcohol, propyl alcohol, butyl alcohol, isobutyl alcohol, t-butyl alcohol, ethylene glycol or propylene glycol. In some embodiments, the aqueous solvent contains isopropyl alcohol.

Suitable reaction conditions for the above semicarbazone-forming processes further include ambient pressure and temperature. Example temperatures can range from about 20 to about 40° C.

The present invention further provides aryl addition processes wherein a compound of Formula VI is prepared by (f) contacting a compound of Formula VII:

with an addition reagent having the formula:

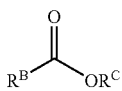

wherein:

each $R^B$ and $R^C$ is, independently, $(C_1-C_4)$alkyl; in the presence of (t-BuO)Y for a time and under conditions sufficient to provide the compound of Formula VI. In some embodiments, Y is an alkali metal such as K. In other embodiments, Y is $Z^1Z^2$, such as, for example, MgBr.

In some embodiments, the reagent (t-BuO)Y can be in excess of the addition reagent. For example, a suitable amount of (t-BuO)Y can be about 1 to about 2 eq relative to the amount of compound of Formula VII.

According to some embodiments, the addition reagent can be ethyl acetate (e.g., $R^B$ is methyl and $R^C$ is ethyl).

The aryl addition processes above can be carried out at ambient or elevated temperatures, such as temperatures above 25° C. Example elevated temperatures can range from about 25 to about 60 or about 30 to about 50° C. Ambient pressure is suitable.

The present invention further provides compounds of Formula II or III:

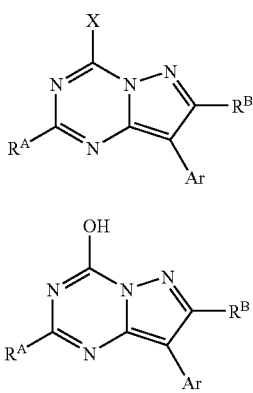

wherein:
Ar is 2-methyl-4-methoxyphenyl, 2-chloro-5-fluoro-4-methoxyphenyl, or 2-methyl-6-methoxypyrid-3-yl;
X is Cl; and
each $R^A$ and $R^B$ is methyl.

The present invention further provides compounds of Formula IV, V, or VI:

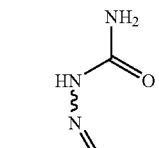
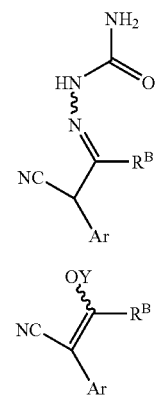

wherein:
Y is an alkali metal or $Z^1Z^2$, wherein:
$Z^1$ is halo; and
$Z^2$ is an alkaline earth metal;
Ar is phenyl or pyridyl substituted with 0 to 5 $R^3$;
each $R^3$ is, independently, H, halo, CN, nitro, $(C_1-C_4)$alkyl, $(C_1-C_4)$alkoxy, $(C_1-C_4)$haloalkyl, or $(C_1-C_4)$haloalkoxy; and
each $R^A$ and $R^B$ is methyl. In some embodiments, the compounds of Formulas IV, V, and VI are substituted wherein Ar is 2-methyl-4-methoxyphenyl, 2-chloro-5-fluoro-4-methoxyphenyl, or 2-methyl-6-methoxypyrid-3-yl. In further embodiments, compounds of Formula VI are provided wherein Y is K.

Scheme I provides an example of a process of preparing pyrazolo[1,5-a]-1,3,5-triazines according to the present invention.

Scheme 1

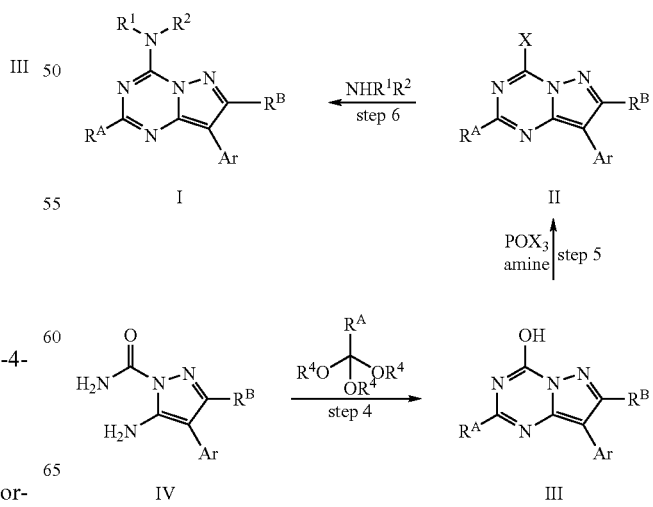

-continued

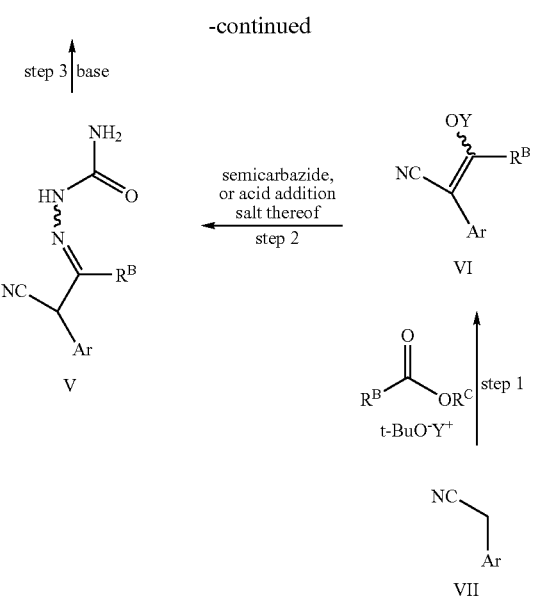

The present invention further provides methods for preparing aryl or heteroaryl acetonitrile derivatives (e.g., compounds of Formula VII) as intermediates in the processes for preparing the CRF antagonist compounds of Formula I. Accordingly, the present invention encompasses processes for preparing compounds of Formula VIII:

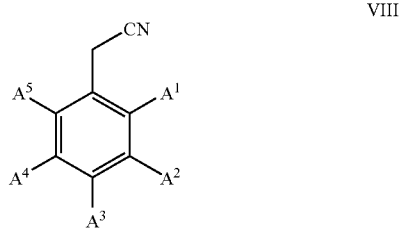

VIII wherein each $A^1$, $A^2$, $A^3$, $A^4$, and $A^5$ is, independently, F, Cl, Br, $(C_1-C_4)$alkyl, $(C_1-C_4)$haloalkyl, $(C_1-C_4)$alkoxy, or $(C_1-C_4)$haloalkoxy;

comprising: (a) contacting a compound of Formula IX:

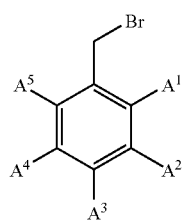

IX with cyanide in the presence of acid for a time and under conditions sufficient to provide the compound of Formula VIII. In some embodiments, $A^1$ is Cl, $A^2$ is H, $A^3$ is methoxy, $A^4$ is F, and $A^5$ is H.

According to some embodiments of the processes for preparing compounds of Formula VIII, the contacting of step (a) can be carried out in the presence of an ammonium salt. Example ammonium salts include benzyltrialkylammonium salts such as benzyltributylammonium chloride, benzyltrialkylammonium, or tetraalkylammonium salts. Ammonium salt can be provided in an amount of about less than 1 eq, or less than 0.1 eq (versus the compound of Formula IX).

In further embodiments of the processes for preparing compounds of Formula VIII, the cyanide in the contacting of step (a) can be provided as a cyanide salt such as sodium or potassium cyanide. Acetone cyanohydrin may also be used. Cyanide can be provided in an amount of about 1 equivalent or greater (versus the compound of Formula IX). In some embodiments, about 3 to 4 equivalents of cyanide is provided.

In even further embodiments of the processes for preparing compounds of Formula VIII, prior to said contacting of step (a), the compound of Formula IX can be dissolved in organic solvent and the cyanide and ammonium salt can be dissolved in aqueous solvent. Accordingly, contacting can be carried out such that individual reagents are dissolved in non-miscible (or weakly miscible) solvents, creating a two-phase reaction system. Any combination of non-miscible solvents can be suitable, so long as the reagents are sufficiently soluble. An example of a non-miscible solvent combination that can form a two-phase system is the combination of organic solvent and water. Example organic solvents that are not miscible in water include, pentane, hexanes, benzene, toluene, diethyl ether, or mixtures thereof. The non-miscible solvent combination in the presence of an ammonium salt catalyst forms the basis of phase transfer catalysis (PTC). PTC is well understood, by those knowledgeable in the art, to have a significant enhancement in the rate of formation of compounds such as compound of Formula VIII. In some embodiments, the two-phase system includes toluene and water. For example, the compound of Formula IX can be dissolved in toluene and the cyanide and ammonium salt can be dissolved in water.

In yet further embodiments of the processes for preparing compounds of Formula VIII, the acid in the contacting of step (a) may be a weak carboxylic acid, such as propionic, butyric, or isobutyric acid. A preferred example acid is acetic acid. The acid can be provided in an amount of about less than one equivalent (versus the compound of Formula IX). An example amount is about 0.3 to about 0.4 eq.

The above processes for preparing compounds of Formula VIII can be carried out at ambient or elevated temperatures, such as temperatures above 25° C. Example elevated temperatures can range from about 25 to about 40 or about 30 to about 40° C. Ambient pressure is suitable.

According to some embodiments, compounds of Formula IX can be prepared by (b) contacting a compound of Formula X:

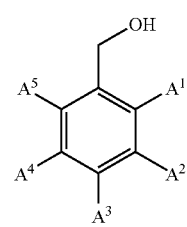

X with HBr for a time and under conditions sufficient to provide the compound of Formula IX. A suitable amount of HBr can be greater than one equivalent (relative to the compound of Formula X) greater than 10 equivalents, or between about 10 and 20 equivalents.

The contacting of step (b) involving compounds of Formula X and HBr can be carried out at any suitable temperature and pressure. Initial contacting can be carried out at low temperatures, such as from about 0 to about 20 C or about 0 to about 15 C and then later raised to higher temperatures such as from about 25 to about 60° C. or about 30 to about 55° C. Ambient pressure is suitable. The compound of Formula X can be dissolved in any suitable solvent system. Example solvents include organic solvents, such as those that are not miscible in water.

In further embodiments, the compound of Formula X can be prepared by (c) contacting a compound of Formula XI:

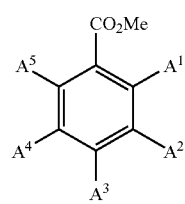

XI with reducing agent for a time and under conditions sufficient to provide the compound of Formula X. Any suitable reducing agent can be used. The amount of reducing agent can be about one or more reducing equivalents. Example reducing agents include bis(2-methoxyethoxy) aluminum hydride (Red-Al), lithium aluminum hydride, lithium borohydride, aluminum borohydride, borane, aluminum hydride, lithium triethyl borohydride, sodium borohydride with appropriate activating ligands and certain enzymes. In some embodiments, the reducing agent is sodium bis(2-methoxyethoxy) aluminum hydride (Red-Al).

Suitable solvent systems for the contacting of step (c) in preparing compounds of Formula X, can be, for example, organic solvents that are inert to strong reducing agents. Example solvents include benzene, toluene, diethyl ether, tetrahydrofuran, pentane, hexanes, mixtures thereof, and the like. In some embodiments, a suitable solvent is toluene.

The contacting of step (c), involving compounds of Formula XI, can be carried out at any suitable temperature. Some suitable temperatures fall below 25 C, including temperatures ranging from about 0 to about 20, about 10 to about 20, or about 14 to about 17° C. Ambient pressure is suitable.

The present invention also provides compounds of Formula VIII, IX, or X:

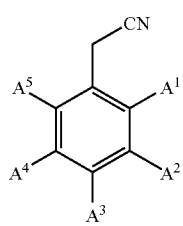

VIII

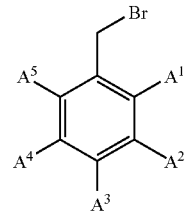

IX

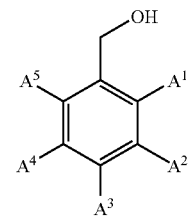

X wherein $A^1$ is Cl, $A^2$ is H, $A^3$ is methoxy, $A^4$ is F, and $A^5$ is H.

An example process of preparing compounds of Formula VIII is provided below in Scheme II.

Scheme II

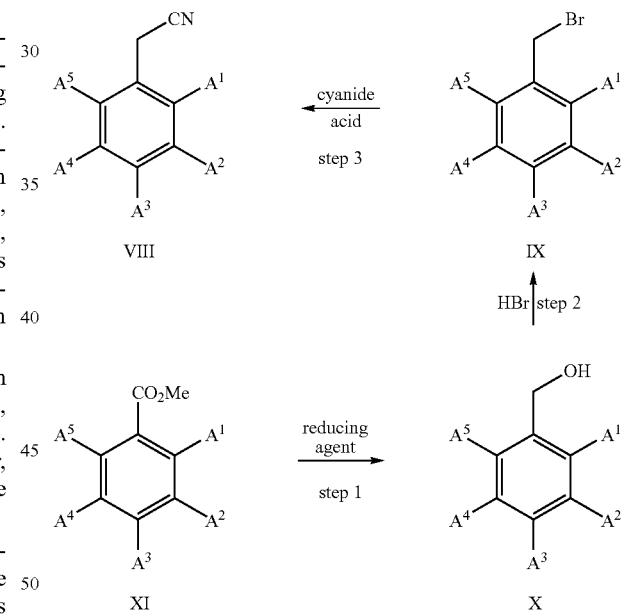

The present invention also provides processes for preparing compounds of Formula XI:

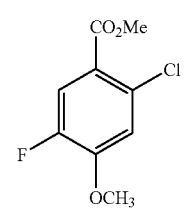

XI comprising (a) contacting a compound of Formula XII:

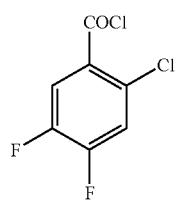

XII with methoxide for a time and under conditions sufficient to provide the compound of Formula XI. Methoxide can be provided in an amount greater than about 2 eq (versus the compound of Formula XII). An example amount of methoxide is about 3 eq. Suitable solvent systems include methanol. Ambient temperature and pressure is also suitable.

In some embodiments, compounds of Formula XII can be prepared by (b) contacting a compound of Formula XIII:

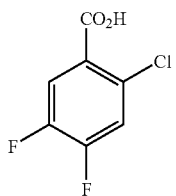

XIII with oxalyl chloride or thionyl chloride for a time and under conditions sufficient to provide the compound of Formula XII. Oxalyl chloride or thionyl chloride can be provided in an amount of at least about one equivalent (versus the compound of Formula XIII). An example amount of oxalyl chloride or thionyl chloride is about 2 eq.

In some embodiments, the contacting of step (b) in the preparation of compounds of Formula XII is carried out in the presence of DMF. DMF can be provided in an amount that is less than one equivalent (eq) (versus the compound of Formula XIII). Example amounts of DMF include between about 0.3 and about 0.6 eq.

Additionally, the contacting of step (b) in the preparation of compounds of Formula XII can be carried out in the presence of organic solvent, such as dimethylformamide (DMF), toluene, or mixtures thereof, or any other solvent that are non-reactive with the reagents.

Suitable temperatures for preparing compounds of Formula XII can be less than about 25° C. In some embodiments, the initial temperature at which the contacting of step (b) is carried out is below 25° C. and which is then raised to above 25° C. at a later point in time, such to a temperature from about 40 to about 60° C. Excess oxalyl chloride can be removed by distillation according to known procedures.

The present invention further provides a compound of Formula XI:

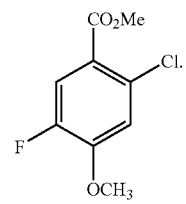

XI

Processes for preparing compounds of Formula XI are illustrated in Scheme III.

Scheme III

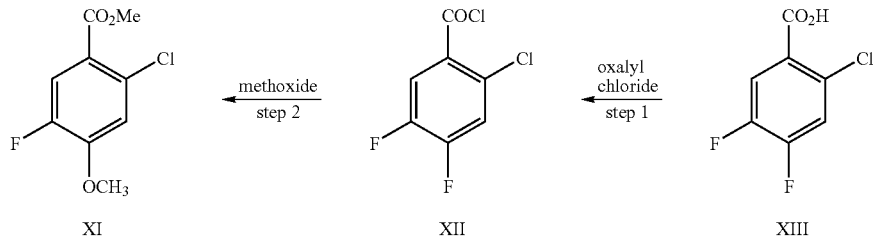

The present invention further provides processes for preparing compounds of Formula XIV:

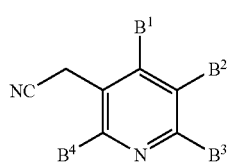

XIV wherein each $B^1$, $B^2$, $B^3$ and $B^4$ is, independently, F, Cl, Br, $(C_1\text{-}C_4)$alkyl, $(C_1\text{-}C_4)$haloalkyl, $(C_1\text{-}C_4)$alkoxy, or $(C_1\text{-}C_4)$haloalkoxy. In some embodiments, $B^1$ is H, $B^2$ is H, $B^3$ is methoxy, and $B^4$ is methyl.

The processes of preparing compounds of Formula XIV comprise contacting a compound of Formula XV:

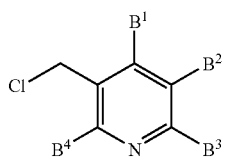

XV

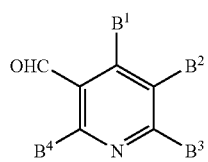

XVII

According to some embodiments, the compounds of Formula XVI are prepared by contacting a compound of Formula XVII:

with cyanide for a time and under conditions sufficient to provide the compound of Formula XIV. Any source of cyanide is suitable. In some embodiments, the cyanide is provided as sodium cyanide. The cyanide reagent can also be provided in an amount that is about one or more equivalents relative to the compound of Formula XV. In some embodiments, the about 3 to about 4 equivalents of cyanide are provided.

The contacting of step (a) for preparing compounds of Formula XIV can be optionally carried out in the presence of an iodide salt. Any iodide salt is suitable, including for example, sodium or potassium salts. Iodide can be provided in a catalytic amount, such as less than one equivalent relative to the compound of Formula XV. In some embodiments, about 0.1 eq of iodide is provided.

In the preparation of compounds of Formula XIV, the contacting of step (a) can be carried out at any suitable temperature or pressure. In some embodiments, contacting is carried out at ambient temperature and pressure.

In some embodiments, the Formula XV can be prepared by (b) contacting a compound of Formula XVI:

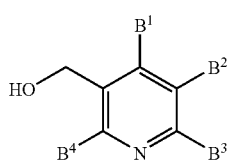

XVI with a chlorinating agent for a time and under conditions sufficient to provide the compound of Formula XV. Any chlorinating agent is suitable. In some embodiments, the chlorinating agent is mesyl chloride or thionyl chloride. Mesyl chloride can be provided in an amount of at least about one equivalent relative to the compound of Formula XVI. Thionyl chloride can be provided in an amount of at least about 0.5 equivalents relative to the compound of Formula XV.

In the preparation of compounds of Formula XV, the contacting of step (b) can be carried out in any suitable solvent. In some embodiments, the solvent includes acetonitrile. Any temperature or pressure can be appropriate. In some embodiments, the contacting is carried out at a temperature of from about 0 to about 10° C., or about 0 to about 5° C.

with a reducing agent for a time and under conditions sufficient to provide the compound of Formula XVI. Any reducing agent of sufficient strength is suitable, and can be provided in an amount of at least about one equivalent relative to the compound of Formula XVII. In some embodiments, the reducing agent is NaBH$_4$. NaBH$_4$ can be provided in an aqueous hydroxide solution (e.g., about 10 to about 20 M NaOH).

In the contacting of step (c) for preparing compounds of Formula XVI, suitable solvents include those that are inert to the reducing agent. In some embodiments, the solvent includes alcohol, such as methanol, ethanol, isopropanol, etc., and mixtures thereof.

According to some embodiments, compounds of Formula XVII can be prepared by (d) contacting a compound of Formula XVIII:

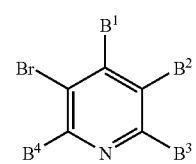

XVIII with n-BuLi followed by a formylating reagent for a time and under conditions sufficient to provide said compound of Formula XVII. The n-BuLi can be provided in an amount of about 1 eq relative to the compound of Formula XVII. Compounds of Formula XVII may also be prepared by contacting a compound of Formula XVIII with a reagent capable of metal-halogen exchange, such as magnesium, lithium, or alkyl lithiums.

Suitable formylating reagents include dimethylformamide (DMF), ethyl formate, N-formylpiperidine, N-methoxy-N-methylformamide. According to some embodiments, the formylating reagent is DMF. The formylating reagent can be provided in an amount of at least about one equivalent (relative to the compound of Formula XVIII). In some embodiments, the formylating reagent is provided in an amount of about two eq.

Suitable solvents for the contacting of step (d) in preparing compounds of Formula XVII are inert to n-BuLi such as, for example, benzene, toluene, hexanes, pentane, and the like. Tetrahydrofuran may also be suitable. Suitable temperatures can range from −80 to about 0° C., such as about −60° C., for initial contacting. Ambient temperature and pressure are suitable after initial contacting.

An example process for the preparation of compounds of Formula XIV is provided in Scheme IV.

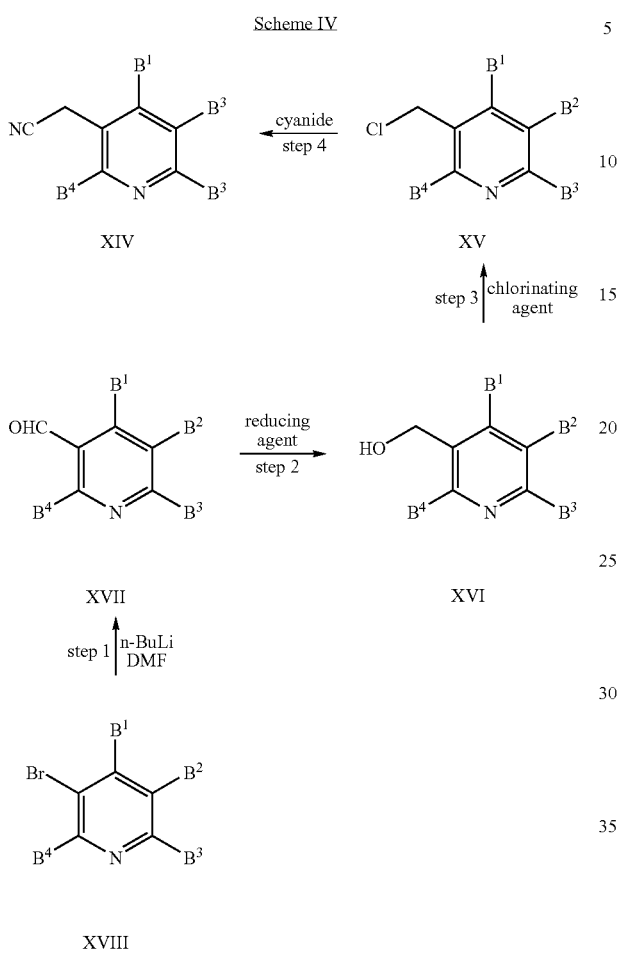

The present invention further provides processes for preparing compounds of Formula XIX:

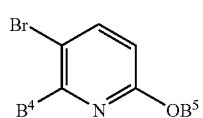

wherein:
B$^4$ is F, Cl, Br, (C$_1$-C$_4$)alkyl, (C$_1$-C$_4$)haloalkyl, (C$_1$-C$_4$)alkoxy, or (C$_1$-C$_4$)haloalkoxy; and
B$^5$ is (C$_1$-C$_4$)alkyl;
comprising:
contacting a compound of Formula XX:

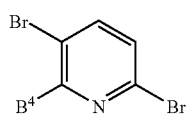

with B$^5$O$^-$ for a time and under conditions sufficient to provide the compound of Formula XIX. According to some embodiments, B$^5$ can be methyl or B$^4$ can be methyl. In further embodiments B$^5$O$^-$ is provided as an alkali salt such as a sodium or potassium salt. The reagent B$^5$O$^-$ can be provided in excess, such as for example greater than 1 eq relative to the amount of compound of Formula XX. The contacting of step (a) can be carried out in any suitable solvent. Some suitable solvents include methanol, benzene, toluene, and the like. Suitable temperatures at which the contacting of step (a) can be carried out include temperatures between about 0 and 120° C. For example, the temperature can be from about 60 to about 80° C. or about 65 to about 75° C. Ambient pressure is suitable.

In further embodiments, the compound of Formula XX can be prepared by (b) contacting a compound of Formula XXI:

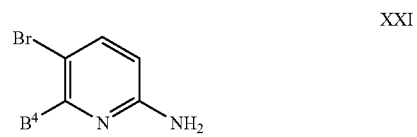

or acid addition salt thereof, with nitrite and Br$_2$ in the presence of acid for a time and under conditions sufficient to provide the compound of Formula XX. In some embodiments, the nitrite can be provided as NaNO$_2$ or HONO. In further embodiments, the acid can be HBr. Each of the nitrite, Br$_2$, and acid can be provided in excess, such as for example, greater than 1 eq relative to the amount of compound of Formula XXI. The contacting of step (b) can be carried out at any suitable temperature. Example temperatures can range from about –10 to about 20, about –5 to about 10, or about 0 to about 5° C.

The reaction mixture resulting from the contacting of step (b) can be further contacted with base to adjust the pH to a value greater than about 7. For example, the hydroxide (such as NaOH, or KOH, etc.) can be added to achieve absolution pH of about 8 to about 14, about 10 to about 14, or about 13.

In some embodiments, the compound of Formula XXI can be prepared by (c) contacting a compound of Formula XXII:

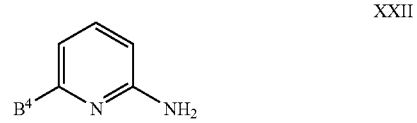

with Br$_2$ in the presence of acid for a time and under conditions sufficient to provide the compound of Formula XXI. In some embodiments, the acid is acetic acid. The contacting of step (c) can be carried out at any suitable temperature and pressure. Some suitable temperatures can be from about 10 to about 25, about 15 to about 20 or about 18° C. Acid can be provided in excess relative to the compound of Formula XXII and can serve as solvent. Bromine (Br$_2$) can be provided in an amount of about 0.5 to about 1.5, about 0.9 to about 1.1 or about 1.0 eq relative to the compound of Formula XXII.

The present invention further provides compounds of Formula XIV or XV:

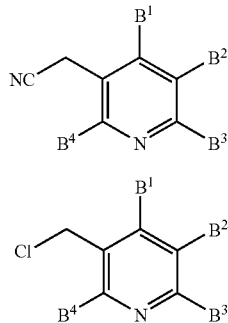

wherein $B^1$ is H, $B^2$ is H, $B^3$ is methoxy, and $B^4$ is methyl.

An example process for the preparation of compounds of Formula XIX is provided in Scheme V.

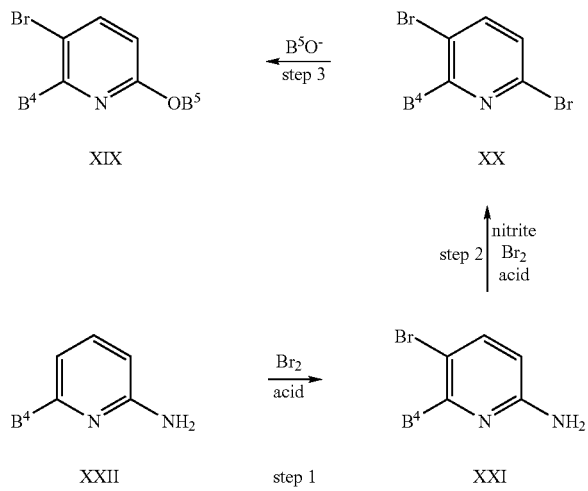

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The term "contacting" as used herein refers to the bringing together of reagents to within distances sufficient to effect molecular transformation such as bond breakage and formation. The reagents provided for contacting can be in any form, such as gas, liquid, solid, or in solution.

The reactions of the processes described herein can be carried out in suitable solvents, such as organic or aqueous solvents, which may be readily selected by one of skill in the art of organic synthesis. Suitable solvents can be substantially non-reactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable organic solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane, hexafluoroethane, 1-chlorobutane, and 1,2-dichloroethane.

Suitable organic solvents include ethers such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, di-n-butyl ether, 2-methyltetrahydrofuran, or 1,3-dioxolane.

Suitable protic solvents may include, by way of example and without limitation, water, or organic solvents such as methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, or 1-methoxy-2-propanol.

Suitable aprotic solvents may include, by way of example and without limitation, the organic solvents tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, hexamethylphosphoramide, n-propyl acetate, isopropyl acetate, n-butyl acetate, ethyl propionate, 2-pentanone, or methyl iso-butyl ketone.

Suitable organic solvents include hydrocarbons such as benzene, cyclohexane, pentane, hexane, toluene, cycloheptane, methylcyclohexane, heptane, ethylbenzene, m-, o-, or p-xylene, octane, indane, nonane, or naphthalene.

As used herein, suitable acids include, but are not limited to hydrochloric acid, hydrobromic acid, sulfuric acid, phosphoric acid, nitric acid, and organic acids.

Suitable organic acids include formic acid, acetic acid, propionic acid, butanoic acid, methanesulfonic acid, p-toluene sulfonic acid, benzenesulfonic acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

As used herein, suitable bases include, but are not limited to: lithium hydroxide, sodium hydroxide, potassium hydroxide, lithium carbonate, sodium carbonate, potassium carbonate, magnesium hydroxide, calcium hydroxide, calcium carbonate, sodium bicarbonate and potassium bicarbonate.

As used herein, suitable strong bases include, but are not limited to, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The compounds described herein may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. Methods on how to prepare optically active forms from optically active starting materials are known in the art, such as by resolution of racemic forms or by synthesis. All chiral, diastereomeric, racemic forms and all geometric isomeric forms of a structure are intended.

The present invention includes all isotopes of atoms occurring in the intermediates or final compounds. Isotopes include those atoms having the same atomic number but different mass numbers. For example, isotopes of hydrogen include tritium and deuterium.

When any variable occurs more than one time in any constituent or in any formula, its definition on each occurrence is independent of its definition at every other occurrence. Thus, for example, if a group is shown to be substituted with 0-3 $R^Z$, then the group may optionally be substituted with up to three different $R^Z$.

The term "substituted", as used herein, means that any one or more hydrogen on the designated atom is replaced with a selection from the indicated group, provided that the designated atom's normal valency is not exceeded, and that the substitution results in a stable compound.

The term "alkyl" as used herein is meant to refer to a saturated hydrocarbon group which is straight-chained, branched or cyclized ("cycloalkyl"). Alkyl groups can be unsubstituted or substituted so that one or more of its hydrogens are replaced by another chemical group. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), cyclopentyl, cyclohexyl, norbornyl, and the like. "Alkenyl" refers to alkyl groups having one or more double carbon-carbon bonds. Example alkenyl groups include ethenyl, propenyl, cyclohexenyl, and the like. "Alkynyl" refers to alkyl groups having one or more triple carbon-carbon bonds. Example alkynyl groups include ethynyl, propynyl, and the like. "Haloalkyl" refers to branched, straight-chained, and cyclyl alkyl groups having one or more halogen substituents. Example haloalkyl groups include $CF_3$, $C_2F_5$, $CHF_2$, $CCl_3$, $CHCl_2$, $C_2Cl_5$, and the like. The "alkoxy" refers to an —O-alkyl group. Example alkoxy groups include, methoxy, ethoxy, propoxy (e.g., n-propoxy and isopropoxy), t-butoxy, and the like. "Haloalkoxy" refers to an alkoxy group substituted by one or more halogens. The term "cycloalkyl" refers to cyclized alkyl groups, including mono-, bi- or poly-cyclic ring systems. Example cycloalkyl groups include cyclopropyl, cyclobutyl, cyclopentyl, cyclohexyl, and so forth. "Halo" or "halogen" includes fluoro, chloro, bromo, and iodo.

"Aryl" groups refer to monocyclic or polycyclic aromatic hydrocarbons, including, for example, phenyl, naphthyl, anthracenyl, phenanthrenyl, indanyl, indenyl, and the like. Aryl moieties are well known and described, for example, in *Hawley's Condensed Chemical Dictionary* (13 ed.), R. J. Lewis, ed., J. Wiley & Sons, Inc., New York (1997), which is incorporated herein by reference in its entirety. Aryl groups can be substituted or unsubstituted.

"Heteroaryl" groups are monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. Heteroaryl groups can be substituted or unsubstituted.

"Heterocyclyl" groups can be saturated (i.e., containing no double or triple bonds) or unsaturated (i.e., containing one or more double or triple bonds) carbocyclyl groups wherein one or more of the ring-forming carbon atoms of the carbocyclyl group is replaced by a heteroatom such as O, S, or N. Heterocyclyl groups can be substituted or unsubstituted. Examples of heterocyclyl groups include morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, and the like. Some example heterocyclyl substituents can include $C_1$-$C_6$ alkyl, $C_3$-$C_6$ cycloalkyl, $C_2$-$C_6$ alkenyl, $C_2$-$C_6$ alkynyl, halogen, $C_1$-$C_4$ haloalkyl, CN, $OR^7$, SH, $NO_2$, $OCF_3$, $S(O)_nR^7$, $COR^7$, $CO_2R^7$, $OC(O)R^7$, $NR^7COR^8$, $N(COR^7)_2$, $NR^7CONR^7R^8$, $NR^7CO_2R^8$, $NR^7R^8$, or $CONR^7R^8$, wherein $R^7$ and $R^8$ are as defined above according to the first aspect of the invention. Heterocyclyl groups can be substituted with any number of substituents such as, for example, 0 to 7, 0 to 6, 0 to 5, 0 to 4, 0 to 3, 0 to 2, or 0 to 1 substituents.

The compounds prepared by the methods described herein can be used to treat disorders characterized by abnormal levels of corticotropin releasing factor (CRF) in mammals.

Some disorders characterized by abnormal levels of corticotropin releasing factor include mood disorders such as depression, including major depression, single episode depression, recurrent depression, child abuse induced depression, seasonal affective disorder, postpartum depression, dysthemia, bipolar disorders, and cyclothymia; anxiety disorders including panic, phobias, obsessive-compulsive disorder; post-traumatic stress disorder; and sleep disorders induced by stress; inflammation; pain; chronic fatigue syndrome; stress-induced headache; cancer; human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ileus, and colonic hypersensitivity associated by psychopathological disturbances or stress; eating disorders such as anorexia and bulimia nervosa; supranuclear palsy; amyotrophic lateral sclerosis; immune suppression; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular disorders including hypertension, tachycardia and congestive heart failure; stroke; immune dysfunctions including stress-induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism; hypoglycemia; hair loss; abnormal circadian rhythm; and disorders related to abnormal circadian rhythm such as time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia, and abnormal circadian rhythm associated with chronic administration and withdrawal of antidepressant agents. Thus, the compounds provided herein, because of their antagonism of CRF receptors, are expected to be useful in treating these and other disorders.

Compounds prepared by the process of the present invention can be administered to treat the above disorders by any suitable means that allows the compound to contact the compound's site of action, such as a CRF receptor, in the body of a mammal. The compounds can be administered by any conventional means available for use in conjunction with pharmaceuticals either as an individual therapeutic agent or in combination with other therapeutic agents. Compounds can be administered alone, or in combination with a pharmaceutical carrier selected on the basis of the chosen route of administration and standard pharmaceutical practice.

The dosage of compound administered varies depending on several factors such as the pharmacodynamic character of the particular compound, and its mode and route of administration; the recipient's age, weight, and health; nature and extent of symptoms; kind of concurrent treatment; frequency of treatment; and desired effect. For use in the treatment of the above diseases or conditions, the compounds of this invention can be orally administered daily at a dosage of the active ingredient (e.g., a compound of Formula I) of about 0.002 to about 200 mg/kg of body weight. For example, a dose of about 0.01 to about 10 mg/kg can be divided into smaller doses and administered one to four times a day. Alternatively, sustained release formulations can be effective in obtaining the desired pharmacological effect.

Dosage forms (compositions) suitable for administration can contain from about 1 mg to about 100 mg of active ingredient per dosage unit. In these pharmaceutical compositions, the active ingredient (e.g., a compound of Formula I) can be present in an amount of about 0.5 to 95% by weight based on the total weight of the composition.

The active ingredient (e.g., a compound of Formula I) can be administered orally in solid dosage forms such as capsules, tablets and powders, or in liquid forms such as elixirs, syrups, and/or suspensions. The compounds can also be administered parenterally in sterile liquid dose formulations.

Gelatin capsules can be used to contain the active ingredient and a suitable carrier such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can also contain coloring or flavoring agents to increase patient acceptance.

Typically, water, pharmaceutically acceptable oils, saline, aqueous dextrose, and related sugar solutions and glycols, such as propylene glycol or polyethylene glycol, are suitable carriers for parenteral solutions. Solutions for parenteral administration can contain, for example, a water soluble salt of the active ingredient and suitable stabilizing agents. Antioxidizing agents, such as sodium bisulfite, sodium sulfite, or ascorbic acid, either alone or in combination, can act as suitable stabilizing agents. Also suitable as stabilizing agents are citric acid and its salts, and EDTA. In addition, parenteral solutions can contain preservatives such as, for example, benzalkonium chloride, methyl- or propyl-paraben, and chlorobutanol.

The compounds prepared by the processes described herein can also be used as reagents or standards in the biochemical study of neurological function, dysfunction, and disease.

As those skilled in the art will appreciate, numerous changes and modifications can be made to the preferred embodiments of the invention without departing from the spirit of the invention. It is intended that all such variations fall within the scope of the invention. Throughout this specification, various groupings are employed to conveniently describe constituent variables of compounds and groups of various related moieties. It is specifically intended that each occurrence of such groups throughout this specification include every possible subcombination of the members of the groups, including the individual members thereof.

It is intended that each of the patents, applications, and printed publications mentioned in this patent document be hereby incorporated by reference in its entirety.

EXAMPLES

Example 1

Preparation of 2-(4-methoxy-2-methylphenyl)-3-oxobutyronitrile potassium salt

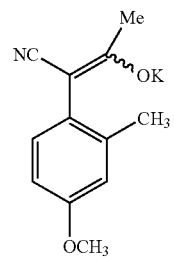

Under anhydrous conditions, (4-methoxy-2-methylphenyl)acetonitrile (25.0 kg, 155 moles, available commercially) and 68.3 kg of ethyl acetate were mixed to obtain a solution. The resulting solution was heated to 35° C. and potassium t-butoxide in THF (100 kg, 20 wt %, 178 moles) was added over a 30 to 60 minute period controlling the temperature at 35° C. Following the addition, the reaction mass was heated to 45° C. and held for 60 minutes. At the end of the hold period, a sample was analyzed by HPLC. The reaction mixture was then cooled to 25° C. and combined with 3 other batches for a total of 843 kg of solution.

Example 2

Preparation of 2-(4-methoxy-2-methylphenyl)-3-oxobutyronitrile semicarbazone

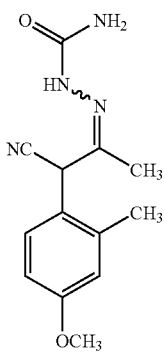

Four batches of the solution prepared according to Example 1 and water (150 kg) were combined. Solvent (557 kg) was distilled from the mixture at 145 mm Hg and 35° C. Next, water (1200 kg), acetic acid (47.0 kg), semicarbazide hydrochloride (89.0 kg, 798 moles) and IPA (475 kg) were added. The resulting mixture was heated to 25-35° C. and held for 21 hours. The reaction was monitored by HPLC. The 2-(4-methoxy-2-methylphenyl)-3-oxobutyronitrile semicarbazone formed was isolated by filtration and the cake washed with water (2×250 kg). A total of 143 kg was isolated. The purity was 99.3 wt %. The yield was 93.1% of theoretical.

Example 3

Preparation of 5-amino-4-(4-methoxy-2-methylphenyl)-3-methylpyrazole-1-carboxylic acid amide

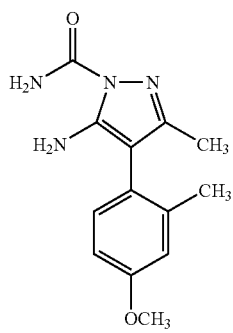

2-(4-methoxy-2-methylphenyl)-3-oxobutyronitrile semicarbazone (160 g, 615 mmol) of Example 2 and N-methylpyrrolidinone (NMP, 480 mL) were charged and the resulting slurry was cooled to <5° C. 1,8-Diazabicyclo[5.4.0]undec-7-ene (DBU, 18.0 mL, 120 mmol) was added. The reaction mass was held at <5° C. for 1.0 to 1.5 hours. Conversion to 5-amino-4-(4-methoxy-2-methylphenyl)-3-methylpyrazole 1-carboxylic acid amide was monitored by HPLC (typically greater than 95%).

Example 4

Preparation of 8-(4-methoxy-2-methylphenyl)-2,7-dimethylpyrazolo[1,5-a][1,3,5]triazin-4-ol

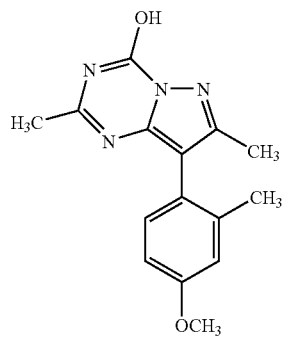

p-Toluenesulfonic acid (29.2 g, 154 mmol) in acetonitrile (100 mL) was added to the reaction mixture described in Example 3 containing 5-amino-4-(4-methoxy-2-methylphenyl)-3-methylpyrazole-1-carboxylic acid amide. The resulting mixture was heated to 85-90° C. and trimethyl orthoacetate (160 mL, 1.26 mol) was added over 5 minutes during the heating. The reaction was held for about 45 minutes in the desired range with a total of 1.5 hours of heating time from the initiation of the heating cycle. Reaction progress was monitored by HPLC. Water (1.50 L) was added over 5 minutes with a temperature drop to about 60° C. The resulting mixture was cooled to about 20° C. over 1 hour and the product isolated by filtration. The yield was 136 g (78.0% with a purity of 99.5 A %).

Example 5

Preparation of N,N-bis(2-methoxyethyl)-8-(4-methoxy-2-methylphenyl)-2,7-dimethylpyrazolo[1,5-a][1,3,5]triazin-4-amine benzenesulfonate

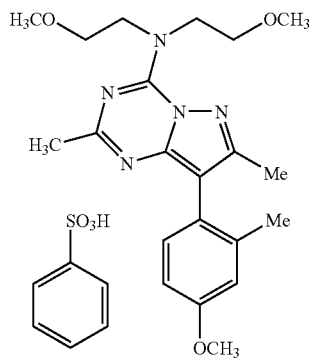

8-(4-Methoxy-2-methylphenyl)-2,7-dimethylpyrazolo[1,5a][1,3,5]triazin-4-ol of Example 4 (6.50 kg, 22.5 mol), benzyltributylammonium chloride (4.70 kg, 15.0 mol), acetonitrile (6.50 L) and methyl t-butyl ether (26.0 L) were charged and the resulting slurry treated with phosphorous oxychloride (3.30 L, 34.9 mol) and N,N-diisopropylethyl amine (6.00 L, 34.3 mol). The resulting mixture was heated to 50-55° C. and held for about 1.5 hr at which time the reaction was complete.

The resulting solution was cooled to about 0° C. and was treated with bis(2-methoxyethyl)amine (8.50 L, 57.5 mol) while maintaining the batch temperature <25° C. The batch was held for about 1.0 hr and was then treated with a solution of potassium hydroxide (11.4 kg, 203 mol) in water (78.0 L) and held for 3-4 hr. The phases were split and the organic portion was washed with water (32.5 L). Additional methyl t-butyl ether (163 L) was added and the batch was filtered to remove particulate matter. The batch was distilled under reduced pressure to remove water and methyl t-butyl ether to an endpoint of about 47.0 L. The solution was cooled to about 0° C. and filtered to remove particulate matter.

The salt was prepared by first adding acetonitrile (6.11 L) to the batch followed by portion-wise addition of a solution of benzenesulfonic acid (3.58 kg, 22.6 mol) in methyl t-butyl ether (6.50 L) with seeding. The resulting slurry is allowed to form over about 2.0 hrs prior to cooling to about 0° C., where the batch is held for about 30 min before being isolated by filtration. Drying afforded 10.7 kg (83.8% of theory).

Example 6

Preparation of 2-chloro-5-fluoro-4-methoxy-benzoic acid methyl ester

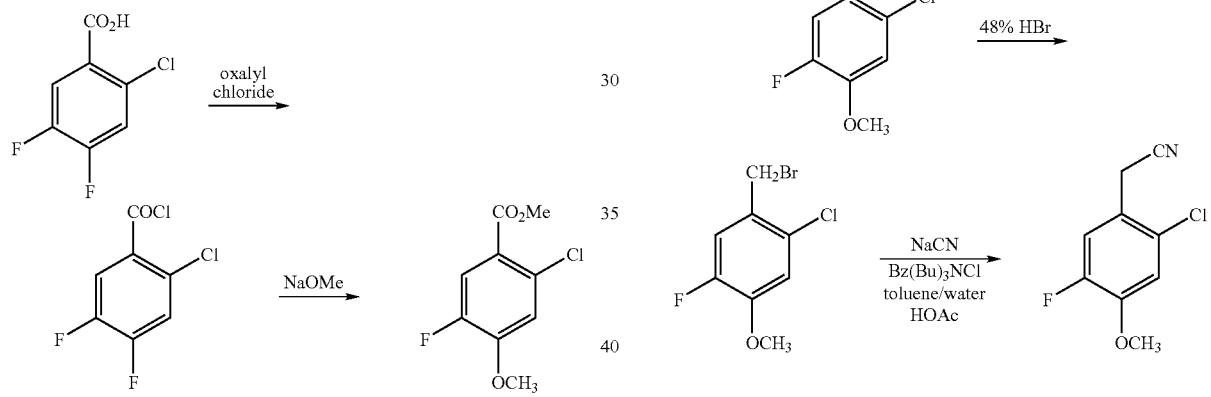

A solution of 2-chloro-4,5-difluoro-benzoic acid (15.0 kg, 99 wgt % purity, 77.1 moles, 1.00 eq) and dimethylformamide (0.2 kg, 2.73 moles, 0.04 eq) in toluene (75.9 kg) was treated with oxalyl chloride (19.8 kg, 156.0 moles, 2.02 eq) while maintaining the temperature at <25° C. over 2 hours. The mixture was heated to 50° C. and held 1 hour. At this point, HPLC indicated reaction completion. Remaining oxalyl chloride was removed by distillation, the pot temperature rising from 85 to 110° C. reflecting the removal of the lower boiling oxalyl chloride until only toluene was distilling. The cooled reaction mass (<25° C.) was transferred to another vessel that contained 25 weight % sodium methoxide in methanol (50.5 kg, 233.7 moles, 3.03 eq) in methanol (90.0 kg). The mixture was stirred overnight at 25° C. and monitored by HPLC. The methanol was removed by distillation at 50° C./150 mmHg vacuum while the volume was maintained by the addition of toluene (total of 184.6 kg added). The distillation was continued until the methanol content by GC was 1.16 v/v %. The resulting solution was washed sequentially (each first stirred for 15 minutes) with water (150.0 kg), 1.6 weight % hydrochloric acid (37.0 kg), aqueous sodium bicarbonate (1.85 kg sodium bicarbonate in 33.15 kg water), and water (35.0 kg). The washed solution was filtered through a 0.2 micron cartridge filter and the volume reduced by half by distillation at 50° C./150 mmHg vacuum. The mixture was heated to 80° C. to redissolve the solids that had appeared and heptane (68.0 kg) was added while maintaining the temperature at 70° C. The slurry was cooled to 5° C. and held overnight. The crystals were collected by filtration, washed with heptane (34.0 kg) and dried at 50° C./50 mmHg to yield 14.4 kg (85% yield) of pure 2-chloro-5-fluoro-4-methoxy-benzoic acid methyl ester product.

Example 7

Conversion of 2-chloro-5-fluoro-4-methoxy-benzoic acid methyl ester to (2-chloro-5-fluoro-4-methoxy-phenyl)-acetonitrile

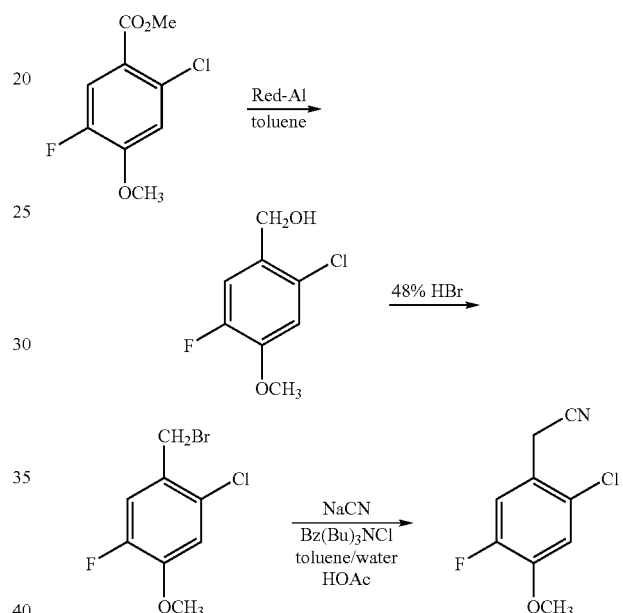

A solution of methyl 2-chloro-5-fluoro-4-methoxybenzoate (2.00 kg of 99.04 wt % material, 9.06 moles, Example 6) in toluene (17.0 L) cooled to 13-15° C. was treated with a 65 wgt % solution of Red-Al (sodium bis(2-methoxyethoxy) aluminum hydride, 2.95 L, 9.83 moles, 1.08 eq) over 1 hour while maintaining the temperature 13-17° C. Sampling by HPLC at this point established that all of the starting material had reacted.

Remaining Red-Al was quenched by the addition of acetone (40 mL). The reaction mass was transferred to a solution of 48% hydrobromic acid (19.0 L, 168 moles, 18.5 eq) previously cooled to 8° C. The addition took 40 min at <50° C. The reaction mixture was heated to 50° C. and held 30 min at which point HPLC indicated 999:1 of 1-bromomethyl-2-chloro-5-fluoro-4-methoxybenzene to (2-chloro-5-fluoro-4-methoxyphenyl)methanol.

The phases were separated and the organic phase washed successively with water five times (2.0 L) until the pH of the aqueous wash reached 5. The solution was filtered through a cartridge filter to produce 18.1 kg of solution, analyzed as 13.17 weight % 1-bromomethyl-2-chloro-5-fluoro-4-methoxybenzene. This intermediate was mixed with acetic acid (195 mL, 3.4 moles, 0.36 eq). A solution of sodium cyanide (1780 g, 36.3 moles, 3.84 eq) and benzyltributyl ammonium chloride (195 g, 0.63 mole, 0.07 eq) in water (7.85 L) was added over 1 minute with vigorous stirring. This mixture was washed in with additional water (2.0 L) and the temperature was adjusted to 35° C. Stirring was continued for 2.5 hours and HPLC sampled to indicate a (2-chloro-5-fluoro-4-methoxy-phenyl)-acetonitrile to 1-bromomethyl-2-chloro-5-fluoro-4-methoxybenzene ratio of 1999:1.

The phases were separated and the organic phase washed with water (18.5 L). This batch was combined with another batch prepared on the same scale. The solution was concentrated by rotary evaporation at <50° C. until the level was ~12 L, at which point the concentration was continued but the level was maintained by the addition of isopropanol. This concentration procedure was continued until GC indicated the toluene content to be 2.09% v/v. A total of 18 L of isopropanol was required. The volume was diluted to 16.5 L with IPA and the solids dissolved by heating. The solution was cooled to 45° C. and the pressure reduced to 120 mmHg to distill out isopropanol while adding water to maintain the volume. The temperature was maintained at 45-50° C. A total of ~15 L water was charged over 5 hours before GC analysis indicated that the isopropanol level had been reduced to 5.7%. The slurry was cooled to ambient temperature overnight and the crystals collected by filtration. The cake was washed with water (5 L) over several washes and the crystals were vacuum dried at 50° C. (25" vacuum) over 4 days to produce 3.533 kg of 99.17 weight % purity (97% corrected yield) of (2-chloro-5-fluoro-4-methoxy-phenyl)-acetonitrile.

Example 8

Preparation of 5-bromo-2-amino-6-picoline HBr salt

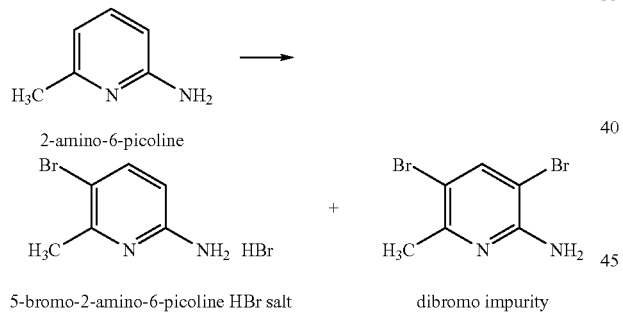

Variation 1

2-Amino-6-picoline (39.8 kg, 99.6 wgt % purity, 367 mol, 1.00 eq) was charged into acetic acid (65.0 kg) while the temperature rose to 60° C. Additional acetic acid (17 kg) was charged to wash in the last of the picoline and the mixture was heated to 35° C. until dissolution occurred. After cooling to 18° C., bromine (56.2 kg, 352 mol, 0.96 eq) was charged at 18±3° C. over 2 hours. More acetic acid (2.0 kg) was charged to wash in the last of the bromine. The mixture was held at this temperature range for 1 hour and then cooled to 11-15° C. It was held in this range for 0.5 hours. The solids were recovered by filtration on polypropylene and washed with isopropanol (63.0 kg) to produce 69.6 kg of moist 5-bromo-2-amino-6-picoline hydrobromide (76 wgt % of product as hydrobromide). This corresponds to a 54% yield. Part of this product was dried for the purposes of recording the $^{13}$C NMR spectrum: $^{13}$C NMR (400 MHz, DMSO-$d_6$) δ 154.1, 146.9, 112.4, 105.2, 20.1.

Variation 2

2-Amino-6-picoline (16.0 kg, 99.6 wgt % purity, 147 mol, 1.00 eq) was charged into acetic acid (35.0 kg) while the temperature was maintained <50° C. Additional acetic acid (2 kg) was charged to wash in the last of the picoline and the mixture was heated to 35° C. until dissolution occurred. After cooling to 18° C., bromine (23.0 kg, 144 mol, 0.98 eq) was charged at 18±3° C. over 2 hours. More acetic acid (2.0 kg) was charged to wash in the last of the bromine. The mixture was held at this temperature range for 1 hour and water (41 L) was charged. The pH was adjusted to 4.0 with 30% sodium hydroxide (35 kg) and the solids were collected on a polypropylene bag on a centrifuge (additional recovery of product from these solids described below). The solids were washed with water (50 L). All of the filtrate and washes were refiltered to remove remaining solids (additional recovery of product from these solids described below) and the pH was adjusted to 13.3 with 30% aqueous sodium hydroxide (75 kg). The solids were collected on a polypropylene bag on a centrifuge and were washed with water (50 L). The solids were combined for drying with those recovered as described below.

Additional product was recovered by the recovery of solids that precipitated in the filtrate of the first filtration described above. These solids were dissolved into water (30 L) and the pH was adjusted to 13.5 with 50% aqueous sodium hydroxide (20.0 kg). The solids were filtered in a polypropylene bag on a centrifuge and the solids washed with water (30 L). These were combined with the 5-bromo-2-amino-6-picoline HBr salt isolated beforehand for drying. Meanwhile, the dibromo impurity cake collected by the first filtration was slurried into water (100 L) and filtered in a polypropylene bag on a centrifuge and the solids washed with water (30 L). The filtrate/wash was recharged to the reactor and the pH adjusted to 12.5 with 50% aqueous sodium hydroxide (12.5 L) and more water (150 L). The solids were filtered in a polypropylene bag on a centrifuge and the solids washed with water (60 L). These were combined with the 5-bromo-2-amino-6-picoline HBr salt solids isolated beforehand and all were dried together at 40° C. over 3 days to yield 16.2 kg of solids (95.6 wgt %) or 56% yield.

Example 9

Conversion of 5-bromo-2-amino-6-picoline HBr salt to 2,5-dibromo-6-picoline

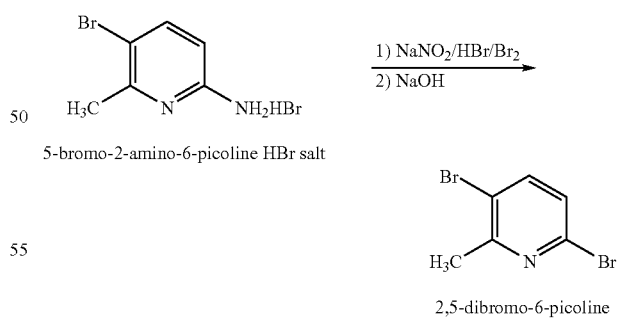

Variation 1

5-Bromo-2-amino-6-picoline hydrobromide (29.4 kg, 76.5 wgt % purity, 84 mol, 1.00 eq) was dissolved into 48% hydrobromic acid (162.0 kg, 961 mol, 11.44 eq) at <35° C. The solution was cooled to 2° C. and bromine (43.0 kg, 269 mol, 3.20 eq) was charged over 40 min. A 40 wt % solution of sodium nitrite (28.9 kg, 419 mol, 4.99 eq) was charged over 50 min at −1 to 5° C. The contents were held one hour and the pH was adjusted to 13.1 using 50% aqueous sodium hydroxide (120.0 kg). The contents were warmed to 20° C. over one hour and toluene (78.0 kg) was charged. The mixture was stirred for 30 min and allowed to settle overnight. The organic phase was clarified by filtration and washed twice with saturated aqueous sodium chloride solution (51.1 kg). This produced 96.0 kg of 2,5-dibromo-6-picoline solution (17.3 wgt %) or 79% yield.

Variation 2

5-Bromo-2-amino-6-picoline (7.0 kg) and 5-bromo-2-amino-6-picoline hydrobromide (7.0 kg) (based on the starting material analyses, this was equal to 11 kg or 41 mol of starting material) are dissolved into 48% hydrobromic acid (107.0 kg, 635 mol, 15.49 eq) at <35° C. The solution was cooled to 2° C. and bromine (27.3 kg, 171 mol, 4.17 eq) was charged over 45 min at 0-5° C. A solution of sodium nitrite (8.1 kg, 117 mol, 2.86 eq) in 20 L of water was charged over 1.5 hours at −1 to 5° C. The contents were held one hour and the pH was adjusted to 12.5 using 50% aqueous sodium hydroxide (70.0 kg). The contents were warmed to 20° C. over one hour and the solids were collected in a polypropylene bag on a centrifuge. The solids were washed with water (75 L) to produce 12.0 kg of moist 2,5-dibromo-6-picoline, determined to be 83 wgt % product (68% yield). Part of this was dried for the purposes of recording the $^{13}C$ NMR spectrum: $^{13}C$ NMR (400 MHz, CDCl$_3$) δ 158.8, 141.9, 139.4, 126.7, 120.6, 24.7.

Example 10

Conversion of 2,5-dibromo-6-picoline to 2-methoxy-5-bromo-6-picoline to 2-methoxy-5-bromo-6-picoline

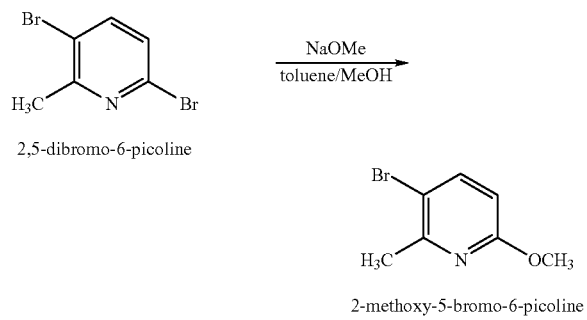

A solution of 2,5-dibromo-6-picoline (30.6 kg, 122 mol, 1.00 eq) in toluene (154.2 kg) was dried by vacuum distillation at 40° C./75 mmHg to remove 105.7 kg of distillate to produce a solution containing 40 ppm water. This was mixed with 25 weight % sodium methoxide in methanol (124.1 kg, 574 mol, 4.71 eq) and the mixture was heated at 65-75° C. for 6 hours until reaction completion, (HPLC analysis indicated 1.6 area % starting material remained). The mixture was cooled to 5° C. and water (98 L) was charged to the mixture followed by t-butylmethylether (97 kg). The layers were separated and the organic phase washed twice with 5% brine (139 kg) and once with 20% brine (165 kg). The organic phase was clarified by filtration and 51 kg was removed by vacuum distillation at 40° C. to produce a 2-methoxy-5-bromo-6-picoline solution (58.4 kg) of 40.6 wt % purity (96% yield). Part of this was purified by distillation for the purposes of recording the $^{13}C$ NMR spectrum: $^{13}C$ NMR (400 MHz, CDCl$_3$) δ 162.4, 154.4, 142.0, 111.8, 109.5, 53.6, 24.6.

Example 11

Conversion of 2-methoxy-5-bromo-6-picoline to benzyl aldehyde derivative

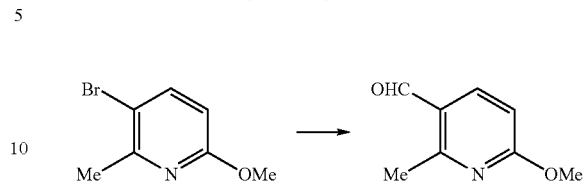

A solution of 2-methoxy-5-bromo-6-picoline (73 wt % solution in toluene, 3.17 kg, 11.45 moles) in THF (18.3 L) was cooled to −60° C. and treated with 2.5 N n-butyllithium in hexanes (4.87 L, 12.2 mol, 1.06 eq). After 0.5 h, dimethylformamide (1.76 L, 22.8 mol, 2.0 eq) was charged at <−50° C. After warming to ambient temperature, an aqueous solution of ammonium chloride (1.6 kg/16.2 L water) was charged and the layers separated. The aqueous phase was re-extracted with methyl t-butylether (3.3 L) and the combined organic extracts were washed with saturated brine (2.5 L). There was a total of 22.4 kg of organic solution (7.08 wt %) corresponding to a 92% solution yield.

Example 12

Conversion of Aldehyde Derivative to Alcohol Derivative

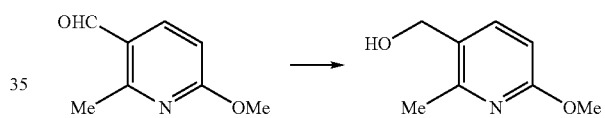

The benzyl aldehyde solution prepared above in Example 11 was solvent exchanged under vacuum to methanol at 25-35° C. This was repeated until the water analysis was <0.1%. The final solution indicated a loss of 7.7% of the benzyl aldehyde. This solution was cooled to 0° C. and a 12 wt % solution of sodium borohydride (12 wt % in 14 M aqueous sodium hydroxide, 660 mL, 2.9 moles, 1.10 eq) was added at 0-5° C. Volatile components were evaporated at <35° C., methyl t-butylether (3 L) added and the evaporation continued. The residue was diluted with methyl t-butylether (4.8 L) and water (3.9 L), and the layers separated. The aqueous phase was further extracted with methyl t-butylether (0.8 L). The combined organic layer consisted of 6.238 kg, (25.16 wt % AJ2153) or a 97.6% solution yield based on the analysis after the solvent exchange.

Example 13

Conversion of Alcohol Derivative to Chloride Derivative

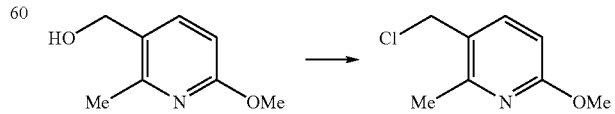

The solution prepared above in Example 12 was solvent exchanged for acetonitrile until the water content was <400 ppm. The solution was diluted with acetonitrile (8.6 L) and cooled to 0-2° C. Thionyl chloride (0.78 kg, 6.6 mol, 0.64 eq) was added at 0-5° C. Most of the volatile components were evaporated at 25-35° C. and the residue dissolved into methyl t-butylether (4.7 L) and saturated sodium bicarbonate solution (4.7 L). Solid sodium bicarbonate (1.41 kg) was added to complete the neutralization. The phases were separated, more water (12 L) was added to the aqueous phase and it was further extracted with methyl t-butylether (2.4 L). The combined organic layers were washed with saturated brine (0.5 L). The organic solution weighed 7.8 kg (16.42 wt %), corresponding to a 72.9% solution yield.

Example 14

Conversion of Chloride Derivative to Nitrile Derivative

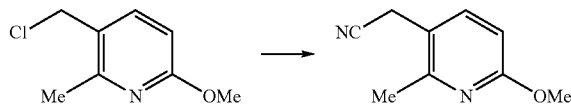

About half the volume of the solution prepared above as described in Example 13 was distilled off and the remainder diluted with isopropanol (7.4 L). A solution of sodium cyanide (1.79 kg, 36.6 moles, 4.9 eq) and sodium iodide (0.11 kg, 0.73 moles, 0.1 eq) in water (4.6 L) was charged. The reaction was stirred until LC indicated a benzyl chloride/benzyl cyanide ratio of 1/100@220 nm. The layers were allowed to settle and the aqueous layer was re-extracted with ethyl acetate (4.2 L). The combined organic solutions were concentrated at 35-40° C. to brown solids. This was dissolved into water (1.5 L) and ethyl acetate (8.2 L) and the layers were separated. The aqueous layer was re-extracted with ethyl acetate (2.6 L) and the combined organic layers washed with a mixture of 1:1 saturated brine plus water (1.3 L). The organic solution was dried with magnesium sulfate (0.26 kg), filtered, and concentrated at 25-35° C. The volume distilled off was replaced with ethyl acetate until the water content was <400 ppm. The weight of the organic solution was 2.68 kg (41.3 wt %). This corresponds to a 91.4% solution yield.

Example 15

Biological Assay

The compounds prepared by the processes of the present invention can have CRF receptor antagonist activity. A compound can be considered active if it has a $K_i$ value of less than about 10,000 nM for the inhibition of CRF. $K_i$ values can be determined by any suitable biological assay, such as, for example, the assay described below.

Provided herein is an example of a $CRF_1$ receptor binding assay that can be used for the evaluation of biological activity of compounds of the present invention. The example also includes isolation of cell membranes containing cloned human $CRF_1$ receptors for use in the binding assay.

Messenger RNA is isolated from human hippocampus by standard techniques. The mRNA is reverse transcribed using oligo (dt) 12-18 and the coding region is amplified by PCR from start to stop codons The resulting PCR fragment is cloned into the EcoRV site of pGEMV, from whence the insert is reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR is transfected in 293EBNA cells, and cells retaining the episome are selected in the presence of 400 µM hygromycin. Cells surviving 4 weeks of selection in hygromycin are pooled, adapted to, growth in suspension, and used to generate membranes for the binding assay described below. Individual aliquots containing approximately $1 \times 10^8$ of the suspended cells are then centrifuged to form a pellet and frozen.

For the binding assay, a frozen pellet described above containing 293EBNA cells transfected with hCRFR1 receptors is homogenized in 10 mL of ice cold tissue buffer (50 mM HEPES buffer pH 7.0, containing 10 mM $MgCl_2$, 2 mM EGTA, 1 µg/l aprotinin, 1 µg/ml leupeptin and 1 µg/ml pepstatin). The homogenate is centrifuged at 40,000×g for 12 min and the resulting pellet rehomogenized in 10 mL of tissue buffer. After another centrifugation at 40,000×g for 12 min, the pellet is resuspended to a protein concentration of 360 µg/ml to be used in the assay.

Binding assays are performed in 96 well plates; each well having a 300 µL capacity. To each well is added 50 µL of test drug dilutions (final concentration of drugs range from $10^{-10}$ to $10^{-5}$ M), 100 µL of $^{125}$I-ovine-CRF ($^{125}$I-o-CRF) (final concentration 150 pM) and 150 µL of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND Munson, et al., *Anal. Biochem.*, 1980, 107, 220, which is incorporate herein by reference in its entirety, which provides $K_i$ values for inhibition which are then used to assess biological activity.

Other in vitro assays for the determination of $CRF_1$ receptor antagonist activity of the present compounds are described, for example, in *Endocrinology*, 1985, 116, 1653 and in *Peptides*, 1985, 10, 179, each of which is incorporated by reference in its entirety. Receptor binding activity of compounds can also be evaluated according to the methods described in Grigoriadis, et al., *Biochemical, Pharmacological, and Autoradiographic Methods to Study Corticotropin-Releasing Factor Receptors. Methods in Neurosciences*, Vol. 5, 1991, which is incorporated herein by reference in its entirety.

Example 16

Inhibition of CRF-Stimulated Adenylate Cyclase Activity

Activity of the present compounds can be studied by the inhibition of CRF-stimulated adenylate cyclase activity which can be performed as described by Battaglia, et al., *Synapse*, 1987, 1, 572, which is incorporated herein by reference in its entirety. Assays are carried out at 37° C. for 10 min in 200 mL of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6}$ M) and 0.8 mg original wet weight tissue (approximately 40-60 mg protein). Reactions are initiated by the addition of 1 mM ATP/[$^{32}$P]ATP (approximately 2-4 mCi/tube) and terminated by the addition of 100 mL of 50 mM Tris-HCL, 45 mM ATP and 2% sodium dodecyl sulfate. In order to monitor the recovery of cAMP, 1 μL of [$^{3}$H]cAMP (approximately 40,000 dpm) is added to each tube prior to separation. The separation of [$^{32}$P]cAMP from [$^{32}$P]ATP is performed by sequential elution over Dowex and alumina columns.

Example 17

In vivo Biological Assay

The in vivo activity of the compounds of the present invention can be assessed using any one of the biological assays available and accepted within the art. Examples of in vivo biological assays for testing axiolytic activity of compounds include the "punished drinking test" (Vogel, et al., *Psychopharmcologia*, 1971, 21, 1, which is incorporated herein by reference in its entirety); "elevated plus-maze test" (Pellow, et al., *J. Neurosci. Methods*, 1985, 14, 149, which is incorporated herein by reference in its entirety); "stress-induced coritcal norepinephrine release" (Funk, et al., *Brain Res.*, 1996, 741, 220, which is incorporated herein by reference in its entirety); "light-dark test" (Misslin, et al., *Behav. Process*, 1989, 8, 119, which is incorporated herein by reference in its entirety); "four-plate test" (Boissier, et al., *Eur. J. Pharmacol.*, 1968, 4, 145, which is incorporated herein by reference in its entirety); and "mouse defense test battery" (Griebel, et al., *Aggress. Behav.*, 1997, 23, 19, which is incorporated herein by reference in its entirety). Compounds may be tested in any species of rodent or small mammal.

Examples of in vivo biological assays for testing antidepressant-like activity of compounds include the "forced swimming test" (Porsolt, et al., *Nature*, 1977, 266, 730, which is incorporated herein by reference in its entirety) and "CMS test" (Willner, et al., *Clin. Neuropharmacol.*, 1992, 15 (supp. 1), 550A, which is incorporated herein by reference in its entirety).

Other models useful for the testing of compounds for their anxiolytic or antidepressant activity are outlined in Berridge, et al., *Brain Research Reviews*, 1990, 15, 71, which is incorporated herein by reference in its entirety. Models for testing activity of compounds for other indications are well known in the art.

What is claimed is:
1. A process for preparing a compound of Formula I:

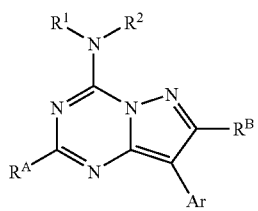

wherein:
Ar is phenyl or pyridyl substituted with 0 to 5 $R^3$;
each $R^1$ and $R^2$ is, independently, H, ($C_1$-$C_8$)alkyl, or ($C_1$-$C_6$)alkoxyalkyl;
each $R^3$ is, independently, H, halo, CN, nitro, ($C_1$-$C_4$)alkyl, ($C_1$-$C_4$)alkoxy, ($C_1$-$C_4$)haloalkyl, or ($C_1$-$C_4$)haloalkoxy; and each $R^A$ and $R^B$ is, independently, ($C_1$-$C_4$)alkyl; comprising:
(a) contacting a compound of Formula III:

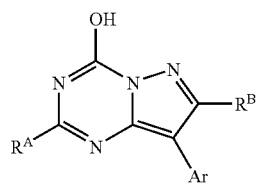

with POX$_3$ in the presence of an ammonium halide salt and an amine selected from diisopropylethylamine, diethylphenylamine, diisopropylaniline, diethylaniline, diisopropylisobutylamine, tribenzylamine, triphenylamine, tricyclohexylamine, or diethylisopropylamine, wherein X is halo, to provide a compound of Formula II:

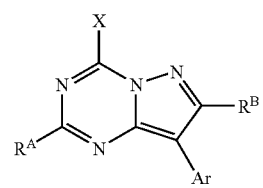

and;
(b) contacting said compound of Formula II with NHR$^1$R$^2$ to provide said compound of Formula I.

2. The process of claim 1 wherein X is Cl.

3. The process of claim 1 wherein said amine is diisopropylethylamine.

4. The process of claim 1 wherein said NHR$^1$R$^2$ is

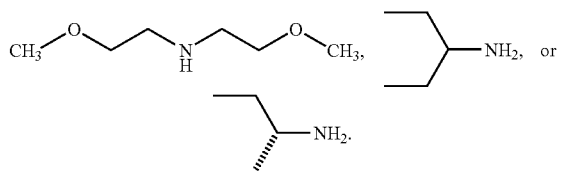

5. The process of claim 1 wherein $R^A$ is methyl.
6. The process of claim 1 wherein $R^B$ is methyl.
7. The process of claim 1 wherein said ammonium halide salt is benzyltriethylammonium chloride, benzyltributylammonium chloride, or methyltrialkyl($C_8$-$C_{10}$)ammonium chloride.
8. The process of claim 1 wherein said ammonium halide salt is benzyltributylammonium chloride.
9. The process of claim 1 wherein said contacting of step (b) is carried out in the presence of organic solvent.
10. The process of claim 9 wherein said organic solvent comprises methyl t-butyl ether, acetonitrile, isopropyl acetate, toluene, or 1-chlorobutane, or mixtures thereof.
11. The process of claim 9 wherein said organic solvent is a mixture of acetonitrile and methyl t-butyl ether.
12. The process of claim 1 wherein said contacting of step (a) is carried out at a temperature of about 50 to about 70° C.
13. The process of claim 1 wherein said compound of Formula II is not isolated prior to said contacting of step (b).

14. The process of claim 1 wherein:
Ar is 2-methyl-4-methoxyphenyl;
$R^1$ is methoxyethyl;
$R^2$ is methoxyethyl;
$R^A$ is methyl; and
$R^B$ is methyl.

15. The process of claim 1 wherein:
Ar is 2-chloro-5-fluoro-4-methoxyphenyl;
$R^1$ is H;
$R^2$ is pent-3-yl;
$R^A$ is methyl; and
$R^B$ is methyl.

16. The process of claim 1 wherein:
Ar is 2-methyl-6-methoxypyrid-3-yl;
$R^1$ is H;
$R^2$ is but-2-yl;
$R^A$ is methyl; and
$R^B$ is methyl.

17. The process of claim 4 wherein said contacting of step (b) is carried out in the presence of acid.

18. The process of claim 17 wherein said acid is acetic acid.

* * * * *